United States Patent [19]
Arhancet et al.

[11] Patent Number: 5,648,574
[45] Date of Patent: *Jul. 15, 1997

[54] COMPOSITIONS AND METHODS FOR INHIBITING VINYL AROMATIC MONOMER POLYMERIZATION

[75] Inventors: Graciela B. Arhancet, Katy; Inge K. Henrici, Spring, both of Tex.

[73] Assignee: BetzDearborn Inc., Trevose, Pa.

[*] Notice: The term of this patent shall not extend beyond the expiration date of Pat. No. 5,510,547.

[21] Appl. No.: 622,133

[22] Filed: Mar. 26, 1996

Related U.S. Application Data

[63] Continuation-in-part of Ser. No. 383,159, Feb. 3, 1995, Pat. No. 5,510,547, which is a continuation-in-part of Ser. No. 118,075, Sep. 8, 1993, Pat. No. 5,396,004, which is a continuation-in-part of Ser. No. 964,321, Oct. 21, 1992, abandoned.

[51] Int. Cl.$^6$ .................. C07C 7/20; C09K 15/16; C09K 15/18
[52] U.S. Cl. .............. 585/5; 585/3; 585/4; 252/402; 252/405; 208/48 AA; 203/8; 203/9
[58] Field of Search ............... 585/3, 5, 4; 252/402, 252/405, 421; 208/48 AA; 203/8, 9

[56] References Cited

U.S. PATENT DOCUMENTS

| | | | |
|---|---|---|---|
| 2,965,685 | 12/1960 | Campbell | 260/666.5 |
| 3,674,651 | 7/1972 | Otsuki et al. | 203/8 |
| 4,105,506 | 8/1978 | Watson | 203/9 |
| 4,409,408 | 10/1983 | Miller | 585/4 |
| 4,466,905 | 8/1984 | Butler et al. | 252/403 |
| 4,720,566 | 1/1988 | Martin | 558/306 |
| 4,774,374 | 9/1988 | Abruscato et al. | 252/402 |
| 4,929,778 | 5/1990 | Roling | 585/3 |
| 4,956,020 | 9/1990 | Nakajima | 134/22.19 |
| 5,396,004 | 3/1995 | Arhancet et al. | 585/5 |
| 5,426,257 | 6/1995 | Arhancet | 585/5 |
| 5,446,220 | 8/1995 | Arhancet | 585/5 |
| 5,489,720 | 2/1996 | Arhancet | 585/5 |
| 5,510,547 | 4/1996 | Arhancet et al. | 585/5 |

FOREIGN PATENT DOCUMENTS

| | | |
|---|---|---|
| 163428 | 11/1971 | Czechoslovakia. |
| 240297 | 2/1987 | European Pat. Off.. |
| 86317087 | 7/1982 | U.S.S.R.. |

*Primary Examiner*—Glenn Caldarola
*Assistant Examiner*—Elizabeth D. Wood
*Attorney, Agent, or Firm*—Alexander D. Ricci; Philip H. Von Neida

[57] ABSTRACT

Compositions and methods for inhibiting the polymerization of vinyl aromatic monomers in oxygen-free processing systems are disclosed. The compositions comprise a hydroxylamine compound, a phenylenediamine compound and a vinyl aromatic monomer. The methods comprise adding to the monomer bis-N,N'(hydroxypropyl) hydroxylamine.

10 Claims, No Drawings

COMPOSITIONS AND METHODS FOR INHIBITING VINYL AROMATIC MONOMER POLYMERIZATION

This is a continuation-in-part of Ser. No. 08/383,159, filed Feb. 3, 1995 now U.S. Pat. No. 5,510,547, which is a continuation-in-part of Ser. No. 08/118,075, filed Sep. 8, 1993, now U.S. Pat. No. 5,396,004, which is a continuation-in-part of Ser. No. 07/964,321, filed Oct. 21, 1992, abandoned.

FIELD OF THE INVENTION

The present invention relates to compositions and methods for inhibiting the undesirable polymerization of vinyl aromatic monomer compounds.

BACKGROUND OF THE INVENTION

Polystyrene is a thermoplastic with many desirable characteristics. It is clear, transparent, readily colored and easily fabricated. The family of styrene polymers includes polystyrene itself, copolymers of styrene with other vinyl monomers, polymers of derivatives of styrene and mixtures of polystyrene and styrene-containing copolymers with elastomers. Pure polystyrene is glass-like, transparent, hard, and rather brittle.

ABS (acrylonitrile, butadiene, styrene) and SAN (styrene, acrylonitrile) resins have enjoyed tremendous commercial popularity for many years as durable, temperature and solvent resistant elastomers. On the other hand, styrene plastics are commonly used for packaging, including foams and films, coatings, in appliance fabrication, for housewares and toys, lighting fixtures and in construction materials.

Common industrial methods for producing vinyl aromatic monomers, such as styrene, include a variety of purification processes, the most common one being distillation. It is well known that vinyl aromatic monomers readily polymerize when heated and that rate of polymerization increases rapidly as the temperature increases. Thermal polymerization during distillation results not only in loss of product, but it could render the finished monomer unsuitable for using without further treatment.

To prevent polymerization of vinyl aromatic monomers under distillation conditions, various inhibitor compositions have been employed. Unfortunately, although several compounds are effective against vinyl aromatic monomer polymerization under storage conditions, only some of these compounds have proved to be effective against polymerization under distillation conditions.

SUMMARY OF THE INVENTION

The present invention relates to compositions and methods for inhibiting polymerization of vinyl aromatic monomers during monomer processing conditions such as distillation of the vinyl aromatic monomers.

The compositions of the present invention are added as a combination of a phenylenediamine compound and a hydroxylamine compound to the vinyl aromatic monomer undergoing processing. The combination is particularly effective at inhibiting polymerization of styrene during its distillation under oxygen-free conditions.

DESCRIPTION OF THE RELATED ART

Dinitrophenol compounds are generally used commercially to inhibit polymerization of vinyl aromatic monomers. U.S. Pat. No. 4,105,506, Watson et al., teaches the use of 2,6-dinitro-p-cresol as a polymerization inhibitor of vinyl aromatic compounds. U.S. Pat. No. 4,466,905, Butler et al., teaches that a combination of 2,6-dinitro-p-cresol and p-phenylenediamine compounds will inhibit polymerization in distillation columns when oxygen is present. U.S. Pat. No. 4,774,374, Abruscato et al., teaches compositions and processes for inhibiting the polymerization of a vinyl aromatic monomer employing the oxygenated reaction product of oxygen and N-aryl-N'-alkyl-p-phenylenediamine compound.

U.S. Pat. No. 4,720,566, Martin, teaches methods and compositions of a hydroxylamine compound and a phenylenediamine compound used for inhibiting the polymerization of acrylonitrile in a quench tower. This system differs from a vinyl aromatic purification process in the type of monomer involved, but also in that oxygen is readily present in an acrylonitrile quench column, the quench tower reactor effluent is cooled by contact with a recirculating water stream and sulfuric acid is added to the quench column.

U.S. Pat. No. 4,929,778, Roling, teaches compositions of a phenylenediamine compound and a hindered phenol compound for inhibiting the polymerization of vinyl aromatic monomers.

U.S. Pat. No. 4,956,020, Nakajima, teaches methods for the inhibition of popcorn polymer, such as styrene, growth in an olefin apparatus. The methods comprise treating the inner surface of an olefin production apparatus with a popcorn polymer growth inhibitor while the operation of the apparatus is suspended and olefins are substantially removed from the apparatus. The popcorn polymer growth inhibitor is selected from the group which can include N,N'-di-sec-butyl-p-phenylenediamine and hydroxylamine.

While these uses may inhibit vinyl aromatic monomer polymerization, it would be advantageous to possess polymerization inhibitors that avoid the use of highly toxic compounds such as dinitrophenol compounds and function in an oxygen-free environment.

DETAILED DESCRIPTION OF THE INVENTION

The present invention relates to compositions for inhibiting the polymerization of vinyl aromatic monomer compounds under processing conditions comprising adding to said monomer an inhibitor composition comprising a hydroxylamine compound and a phenylenediamine compound.

The present invention also relates to a method for inhibiting the polymerization of vinyl aromatic monomer compounds under processing conditions comprising adding to said monomer bis-N,N'(hydroxypropyl)hydroxylamine.

The compositions of the present invention prove efficacious at inhibiting the polymerization of vinyl aromatic monomers, particularly styrene, during their processing. These processing conditions include but are not limited to purification and distillation of vinyl aromatic monomers.

The hydroxylamine compounds useful in this invention generally have the formula:

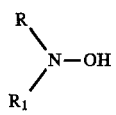

wherein R and $R_1$ are the same or different and are hydrogen, alkyl, aralkyl, or hydroxyalkyl groups and preferably have about 3 to about 20 carbon atoms, except when R is H, then $R_1$ is a $C_6$ to $C_{20}$ alkyl group. The preferred hydroxylamine compounds are N,N'-diethylhydroxylamine (DEHA), isopropylhydroxylamine (IPHA) and bis-N,N'(hydroxypropyl) hydroxylamine (HPHA).

The phenylenediamine compounds useful in this invention generally have the formula:

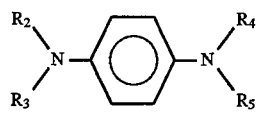

wherein $R_2$, $R_3$, $R_4$, and $R_5$ are the same or different and are hydrogen, alkyl, aryl, alkaryl or aralkyl groups having from 1 to about 20 carbons. The preferred phenylenediamine compound is N,N'-di-sec-butyl-p-phenylenediamine (PDA).

The total amount of hydroxylamine compound and phenylenediamine compound used in the methods of the present invention is that amount which is sufficient to inhibit polymerization and will vary according to the conditions under which the vinyl aromatic monomer is being processed and exposed to high temperatures. At higher temperatures and higher monomer contamination, larger amounts of the polymerization inhibiting composition are required.

Preferably, the total amount of polymerization inhibiting composition added to the vinyl aromatic monomer ranges from a total of 1 to about 10,000 parts per million pads of monomer. More preferably, the range is about 5 parts to about 500 parts of the composition per million parts of monomer. The weight ratio of hydroxylamine compound to phenylenediamine compound present in the vinyl aromatic monomer ranges from 1:9 to 9:1 with a weight ratio of 1:1 preferred.

The amount of bis-N,N'(hydroxypropyl)hydroxylamine added to the vinyl aromatic monomer will vary as per the earlier described conditions. This amount generally ranges from about 1 to about 10,000 parts per million parts of vinyl aromatic monomer. Preferably, this amount ranges from about 100 parts to about 1000 parts per million parts of vinyl aromatic monomer.

The compositions of the present invention can be added to the vinyl aromatic monomer by any conventional method, either as individual components or as a combination. It is preferred that the individual ingredients are added to the monomer as a single treatment.

The compositions of the present invention may be added to the vinyl aromatic monomer as either a dispersion or as a solution using a suitable liquid carrier or solvent. Any solvent that is compatible with the individual ingredients of the composition and the vinyl aromatic monomer may be employed.

Accordingly, it is possible therefor to produce a more effective vinyl aromatic monomer polymerization inhibition treatment than is obtainable by the use of any one ingredient alone when measured at comparable treatment levels. This enhanced activity allows for the concentration of each of these ingredients to be lowered and the total quantity of polymerization inhibitor required, particularly at higher processing temperatures, may be reduced.

This invention will now be further described with reference to a number of specific examples which are to be regarded solely as illustrative and not as restricting the scope of the invention.

EXAMPLES

In order to evaluate the improved polymerization inhibition of the inventive combinations and to demonstrate the enhanced activity of the combination, styrene polymerization testing was performed.

Uninhibited styrene (5 ml) was placed in a test tube and the appropriate amount of treatment was added. The tube was capped with a septum and argon was bubbled through the liquid at 15 ml/min for 3 minutes. Then, the tubes were placed in an oil bath heated to 100° C. for 2 hours. The amount of polystyrene formed was determined by methanol precipitation. Results of this testing are summarized in Table I.

TABLE I

| Styrene Polymerization Test Uninhibited styrene at 100° C. | | |
|---|---|---|
| Treatment | Dose (ppm) | Polymer formed (mg/5 ml) |
| Blank | — | 271 |
| IPHA | 25 | 232 |
| IPHA | 50 | 150 |
| IPHA | 100 | 96 |
| IPHA/PDA | 25/25 | 89 |
| IPHA/PDA | 50/50 | 38 |
| Blank | — | 239 |
| DEHA | 25 | 192 |
| DEHA | 50 | 149 |
| DEHA | 100 | 98 |
| DEHA/PDA | 25/25 | 94 |
| DEHA/PDA | 50/50 | 54 |
| PDA | 100 | 86 |

IPHA is isopropylhydroxylamine
DEHA is N,N'-diethylhydroxylamine
PDA is N,N'-di-sec-butyl-p-phenylenediamine The results of this testing indicate that the composition of hydroxylamine compound and phenylenediamine compound, particularly IPHA/PDA and DEHA/PDA, provides enhanced activity over either hydroxylamine compound at inhibiting the polymerization of styrene. These results are particularly indicative of the compositions enhanced activity at inhibiting the polymerization of styrene under oxygen free conditions and high temperatures which are present when styrene is undergoing processing such as distillation or purification.

The procedure described to generate the examples of Table I was repeated. The results of this testing are presented in Table II.

TABLE II

| Treatment | Dose(ppm) | Polymer (mg/5 ml) |
|---|---|---|
| Blank | — | 174 |
| PDA | 100 | 33 |
| PDA | 50 | 114 |
| PDA | 25 | 130 |
| HPHA | 100 | 70 |
| HPHA | 50 | 105 |
| HPHA | 25 | 141 |
| PDA/HPHA | 50/50 | 22 |
| PDA/HPHA | 25/25 | 60 |

PDA is N,N'-di-sec-butyl-p-phenylenediamine
HPHA is bis-N,N'(hydroxypropyl)hydroxylamine These results demonstrate that the HPHA is effective by itself at inhibiting the polymerization of styrene. These results further demonstrate that HPHA is more effective than either the DEHA or IPHA reported in Table I.

While this invention has been described with respect to particular embodiments thereof, it is apparent that numerous other forms and modifications of this invention will be obvious to those skilled in the art. The appended claims and this invention generally should be construed to cover all such obvious forms and modifications which are within the true spirit and scope of the present invention.

Having thus described the invention, what we claim is:

1. A composition comprising a vinyl aromatic monomer, a hydroxylamine compound and a phenylenediamine compound, wherein the weight ratio of said hydroxylamine compound to said phenylenediamine compound in said vinyl aromatic monomer is from 1:9 to 9:1.

2. The composition as claimed in claim 1 wherein said vinyl aromatic monomer is styrene.

3. The composition as claimed in claim 1 wherein said hydroxylamine compound has the formula:

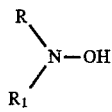

wherein R and $R_1$ are the same or different and are hydrogen, alkyl, aralkyl, or hydroxyalkyl groups and have about 3 to 20 carbon atoms.

4. The composition as claimed in claim 3 wherein R is H and $R_1$ is a $C_6$ to $C_{20}$ alkyl group.

5. The composition as claimed in claim 3 wherein said hydroxylamine compound is N,N'-diethylhydroxylamine.

6. The composition as claimed in claim 3 wherein said hydroxylamine compound is isopropylhydroxylamine.

7. The composition as claimed in claim 1 wherein said phenylenediamine compound has the formula:

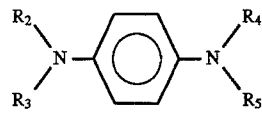

wherein $R_2$, $R_3$, $R_4$ and $R_5$ are the same or different and are hydrogen, alkyl, aryl, alkaryl, or aralkyl groups having from 1 to about 20 carbon atoms.

8. The composition as claimed in claim 7 wherein said phenylenediamine compound is N,N'-di-sec-butyl-p-phenylenediamine.

9. A method for inhibiting the polymerization of vinyl aromatic monomers undergoing processing comprising adding to said monomers an effective polymerization inhibiting amount of bis-N,N'(hydroxypropyl)hydroxylamine.

10. The method as claimed in claim 9 wherein said bis-N,N'(hydroxypropyl)hydroxylamine is added to said monomer in an amount ranging from about 1 parts to about 10,000 parts per million parts of monomer.

* * * * *